United States Patent
Kang et al.

(10) Patent No.: US 7,049,447 B2
(45) Date of Patent: May 23, 2006

(54) AZIRIDINE DERIVATIVES AND THEIR PREPARATION METHODS

(75) Inventors: Jae-Sung Kang, Yongin-si (KR);
Sun-Ki Chang, Kunpo-si (KR);
Kyoung-Mee Seol, Siheung-si (KR);
Min-Kyu Kim, Bucheon-si (KR)

(73) Assignee: Samchully Pharm. Co.,Ltd., Seoul (KR)

( * ) Notice: Subject to any disclaimer, the term of this patent is extended or adjusted under 35 U.S.C. 154(b) by 105 days.

(21) Appl. No.: 10/473,259

(22) PCT Filed: Apr. 19, 2002

(86) PCT No.: PCT/KR02/00713

§ 371 (c)(1),
(2), (4) Date: Sep. 29, 2003

(87) PCT Pub. No.: WO02/085893

PCT Pub. Date: Oct. 31, 2002

(65) Prior Publication Data

US 2004/0097480 A1    May 20, 2004

(30) Foreign Application Priority Data

Apr. 19, 2001   (KR) .................... 10-2001-0021138

(51) Int. Cl.
*C07D 405/04*    (2006.01)
(52) U.S. Cl. ...................................... 548/962
(58) Field of Classification Search ............... 548/962
See application file for complete search history.

(56) References Cited

FOREIGN PATENT DOCUMENTS

KR    P2001-0018263    3/2003
WO    WO 01/12599 A1    2/2001

OTHER PUBLICATIONS

Ichimura, "Synthese der Epimizoucke," Bull. Chem. Soc. Japan, (1970) vol. 43, pp. 2501-2506.*
Kang & Ryu, "A Stereoselective Synthesis of syn-B-Amino Alcohols via iodocyclization," Bull. Korean Chem. Soc. (1996) vol. 17, No. 3, p. 220.*
Shao et al., "A New Asymmetric Synthesis of alpha-Methylcysteines via Chiral Aziridines," J. Org. Chem. (1995) vol. 60, No. 4. pp. 790-791.*
Kang, Sung Ho et al., "A Stereoselective Synthesis of syn-β-Amino Alcohols via Iodocyclization," Bull. Korean Chem. Soc., 1996, vol. 17, No. 3, pp. 219-221.
Ichimura, Kunihiro, "Synthese der Epiminozucker," Bull. of the Chem. Soc. of Japan, Aug. 1970, vol. 43, pp. 2501-2506.
Shao, Hui et al., "A New Asymmetric Synthesis of α-Methylcysteines via Chiral Aziridines," J. Org. Chem., 1995, vol. 60, No. 4, pp. 790-791.

* cited by examiner

*Primary Examiner*—Kamal A. Saeed
*Assistant Examiner*—Andrew B. Freistein
(74) *Attorney, Agent, or Firm*—Henry D. Coleman; R. Neil Sudol; William J. Sapone

(57)    ABSTRACT

The present invention relates to a new aziridine derivative that is represented herein by general chemical formulae (Ia) or (Ib), and to their preparation method. In the said chemical formulae, $R_2$ and $R_3$ can be the same or different, and they are hydrogen, low-quality alkyl or cycloalkyl respectively; $R_4$ can be selected among hydrogen, alkyl, aryl, or amino protective group; and amino protective group is, for example, $(Ph)_3C$, and FMOC(9-fluorenylmethyloxycarbonyl), alkoxycarbonyl, aryloxycarbonyl, aralkyloxycarbonyl and $R_5CO$, $R_5SO_2$ where $R_5$ is alkyl, aryl or aralkyl.

4 Claims, No Drawings

AZIRIDINE DERIVATIVES AND THEIR PREPARATION METHODS

TECHNICAL FIELD

The present invention relates to the preparation methods of aziridine derivatives, and in particular to the preparation methods of aziridine derivatives which are important intermediates for the synthesis of oligopeptide analogues including HIV (Human Immunodeficiency Virus) protease inhibitors.

BACKGROUND ART

The HIV is a retrovirus with RNA-type genetic information. As the medical treatment agents of the virus, there are reverse transcriptase inhibitors and HIV protease inhibitors, etc. However, since almost all the inhibitors are only capable of preventing an infection of cell but not capable of preventing the virus duplication in an infected cell, the inhibitors are generally known as an inhibitor for extending a life span of human slightly rather than curing the disease. Due to the development of a certain virus having tolerance to the compounds, a new curative medicine with a new structure is urgently needed.

The HIV protease inhibitors developed so far are Saquinavir of the Roche company (European Patent 432695 A (1991)), Amprenavir of the Glaxo-Wellcome company (U.S. Pat. No. 941,982 (1992)), Indinavir of the Merck company (U.S. Pat. No. 789,508 (1991)), Ritronavir of the Abbott company (U.S. Pat. No. 998,114 (1992)), and Nelfinavir of the Agouron company (U.S. Pat. No. 5,484,926 (1996)). The compounds are mainly used for treating or preventing the acquired immune deficiency syndrome (AIDS) due to HIV infection.

The HIV protease inhibitors are belonging to an inhibitor referred as a hydroxyethylamine family. The compounds except for Nelfinavir, i.e., Saquinavir, Palinavir and Amprenavir have a benzyl group at the second carbon position in the structure of hydroxyethylamine.

As the intermediates for the synthesis of the HIV protease inhibitor, (2R)-[1'(S)-azido-2-phenylethyl]oxiran (J. Med. Chem. 1993, 36, 292–294), 3(S)-amino-1,2(S)-epoxy-4-phenylbutane, etc. have been known. Since the intermediates are prepared from phenylalanine, they always have benzyl groups at the structure of hydroxyethylamin (HEA). However Nelfinavir has a phenylthiomethyl group instead of a benzyl at HEA, a intermediates with different structures such as 3(S)-amino-1,2(S)-epoxy-4-phenylbutane is necessary.

Therefore, in order to develop a conventional or new HIV protease inhibitor, new intermediates capable of accepting a benzyl group as well as phenylthiomethyl or other substituents are necessary.

DISCLOUSRE OF INVENTION

Accordingly, it is an object of the present invention to provide aziridine derivatives capable of accepting various substituents.

It is another object of the present invention to provide the preparation methods of crucial intermediates for the synthesis of HIV protease.

The present invention relates to aziridine derivatives of the following formula (Ia) or (Ib),

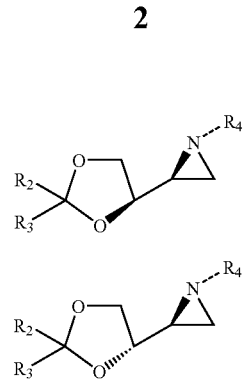

where $R_2$ and $R_3$ may be same or different and respectively represents hydrogen, low alkyl or cycloalkyl, and $R_4$ is selected from the group comprising a hydrogen, alkyl, aryl, aralkyl and amino protecting group. The amino protecting group is $R_5CO$ or $R_5SO_2$, where $R_5$ is selected from the group comprising alkyl, aryl and aralkyl; $CH_3$-Ph-$SO_2$—, $(Ph)_3C$, FMOC(9-fluorenylmethyloxycarbonyl), alkoxycarbonyl, aryloxycarbonyl or araklyloxycarbonyl, preferably t-butoxycarbonyl or benzyloxycarbonyl, and their preparation methods. According to the invention, the derivatives of aziridine with amino group and hydroxy group protected from ascorbic acid, can be prepared. The aziridine derivatives are useful and important intermediates for preparing HIV protease inhibitors.

A preparation method for aziridine derivatives with formula (Ia) and (Ib) is described as follows:

(a) The epoxy compound of the formula (1a) or (1b) where $R_2$ and $R_3$ may be same or different and respectively represents hydrogen or low alkyl group, are reacted with $NaN_3$ for thereby preparing a 1-azido-2-hydroxy-3,4-isopropylidenebutane-2,3,4-triol derivative of formula (2a) or (2b) where $R_2$ and $R_3$ are same as defined above; and (b) the compound of the formula (2a) or (2b) where $R_2$ and $R_3$ are same as defined above, are formed to compounds which have an amine ring structure and being protected by an amino protection group, to prepare aziridine derivatives of the formula (Ia) or (Ib) where $R_2$, $R_3$ and $R_4$ are same as defined above.

The following chemical reaction formula (Ia) illustrates an example of the above method.

[chemical reaction formula 1a]

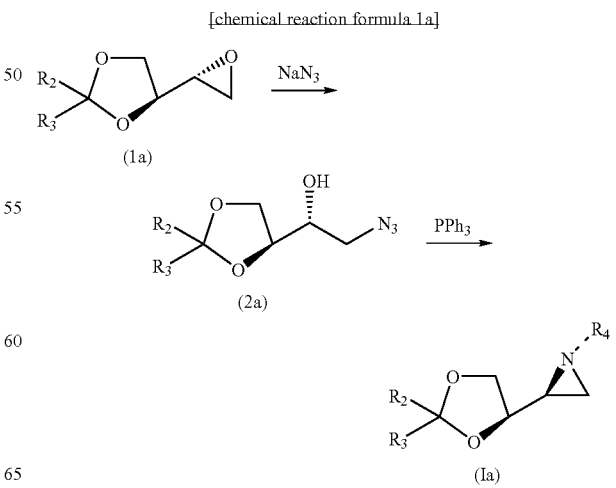

The following chemical reaction formula (Ib) illustrates another example of the above method.

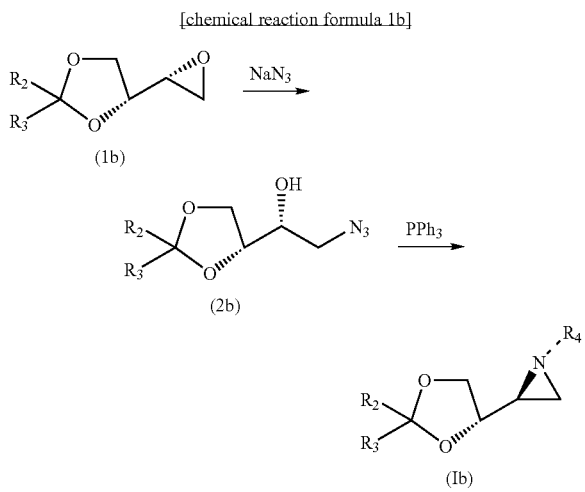

The epoxy compounds of formula (1a) or (1b) can be prepared by the known methods using ascorbic acid as a starting material. The methods are disclosed in J. Org. Chem. 1990, Vol 55, 4400–4403; chem. Soc. Perkin Trans. 1 1995 1783–1785; Tetrahedron Letters 1990, Vol31, No7. 1003–1006; J. Org. Chem. 1988, Vol 53, 2598–2602, etc.

For example, the epoxy compound of formula (1a) may be prepared using a L-ascorbic acid as a starting material, and the epoxy compound of (1b) may be prepared from a D-Isoascorbic acid.

As a solvent, methanol or ethanol/$NH_4Cl$, methylformate, etc. can be used in the step (a) and acetonitrile, toluene, THF, DMF, etc. can be used in the step (b).

The present invention provides the preparation methods for aziridine derivatives of the following formula (II):

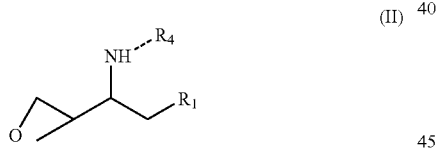

where $R_1$ represents phenyl or phenyl substituted with halogen, alkyl, alkoxy, $ROCOCH_2O$— in which R represents alkyl, or benzyloxy group; phenylthio or alkylthio; heteroaryl with more than one nitrogen, oxygen or sulfur atom; cycloalkyl or cycloalkyl substituted with alkyl group; alkyl or alkenyl with $C_1$–$C_4$ carbon atoms; alkenyl substituted with a phenyl or $OC_4H_6N$—$(CH_2)_2$-Ph-; heterocycle including a nitrogen and/or oxygen; and heterocycle including a nitrogen and/or oxygen with an alkyl group, which are important intermediates for synthesizing HIV protease using an aziridine derivative of the following formula (I),

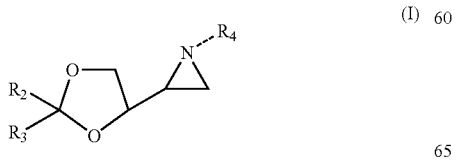

where $R_2$, $R_3$ and $R_4$ have the same definitions as above.

The compound of formula (II) is prepared from an aziridine derivative of formula (I) by the following method.

(a) The compound of the following formula (6) where $R_1$, $R_2$, $R_3$ and $R_4$ have the same definitions as above is prepared by adding $R_1$ to the compound of formula (I), (b) the compound of the following formula (7) where $R_1$, $R_2$, $R_3$ and $R_4$ have the same definitions as above is prepared by removing a hydroxyl protecting group from the compound of formula (6), and (c) an aziridine derivative of the following formula (II) is prepared by epoxidation of the compound of the following formula (7) with the above $R_1$, $R_2$, $R_3$ and $R_4$.

The following chemical reaction formula (II) illustrates the preparation method for the compound of formula (II) which is started from the compound of formula (I).

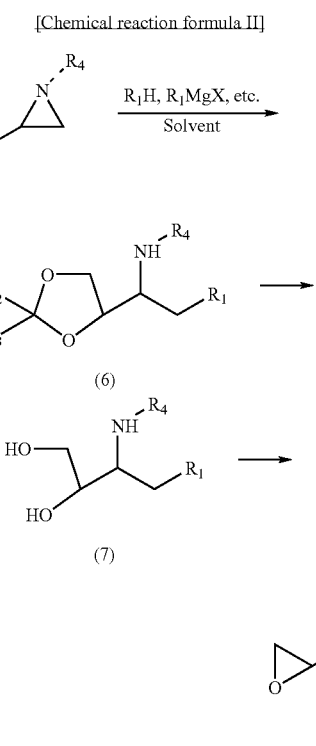

Formula (I) represents the compound of formula (Ia) or formula (Ib). It is possible to prepare various isomers by adjusting the reaction conditions for preparing the compound of formula (II) from the compound of formula (I).

For example, in the case that $R_1$ is phenyl group among the compounds of formula (II), the compound can be a raw material for synthesizing the Amprenavir. In addition, streoisomers which can be used as a PI intermediate of the BMS Co. can be prepared by controlling streochemistry selectively in the step (c) in which the compound of formula (II) where $R_1$ is phenyl group is prepared from the compound of the formula (7).

In addition, in the case that $R_1$ is a phenylthio group, the compound is a synthesizing material of Nelfinavir.

BEST MODE FOR CARRYING OUT THE INVENTION

Now, the invention will be described in detail by the examples.

I. Preparation of an Aziridine Derivative of the Formula (I)

EXAMPLE 1

(2R,3S)1-azido-2-hydroxy-3,4-isopropylidenebutane-2,3,4-triol (2a)

(2S,3R)3,4-epoxy-1,2-O-isopropylidenebutane-1,2-diol (32.9 g) was dissolved in the mixture of 410 ml of ethanol and 40 ml of water. After 85.4 ml of methyl formate was added to the solution, 40 ml of water and 36.9 g of $NaN_3$ were added to the solution. The solution was stirred at 50~60° C. for 6 hours. At the end of the reaction, ethanol was distillated under reduced pressure, and the resultant solution was diluted with 300 ml of water. The resultant solution was extracted using 300 ml of methylene chloride. After the solution was treated with anhydrous $Na_2SO_4$ and distillated under reduced pressure, a light yellow liquid compound of (2R,3S)1-azido-2-hydroxy-3,4-isopropylidenebutane-2,3,4-triol was obtained (40.6 g, yield: 95%).

1H-NMR (300 MHz, $CDCl_3$); δ1.35(s, 3H), 1.42(s, 3H), 2.83(d, 1H), 3.40(dd, 1H), 3.53(dd, 1H), 3.71~3.78(m, 1H), 3.93~4.10(m, 1H)

EXAMPLE 2

(2R,3S)1,2-O-isopropylidene-3,4-(t-butoxycarbonyl (imino-butane-1,2-diol (Ia)

(2R,3S)1-azido-2-hydroxy-3,4-isopropylidenebutane-2,3,4-triol (40.6 g) was dissolved in 800 ml of acetonitrile and $PPh_3$ of 56.9 g (1 equivalent) was added to the solution. The solution was stirred at a room temperature for 1 hour and refluxed for 12 hours at an increased temperature. The solution was cooled down to room temperature and distillated under reduced pressure. 200 ml of 1,4-dioxane and 200 ml of water were added to the solution and 36.4 g of $NaHCO_3$ (2 equivalents) was added to the solution. Thereafter, $(Boc)_2O$ of 50.4 ml (1 equivalent) was added. After the resultant solution was stirred at room temperature for 1 hour, the solvent was distillated under reduced pressure. And then the solution was diluted with 250 ml of diethyl ether and was washed with 250 ml of water. The separated ether layer was treated with $Na_2SO_4$ anhydride and distillated under reduced pressure. A white liquid compound of (2R,3S)-1,2-O-isopropylidene-3,4-(t-butoxycarbonyl)imino-butane-1,2-diol was obtained (50 g, yield: 95%).

$[\alpha]_D^{25}$=−72.19 (Cl, $CHCl_3$) 1H-NMR (300 MHz, $CDCl_3$): δ1.35(s, 3H), 1.44(s, 3H), 1.46(s, 9H), 2.13(d, 1H), 2.28(d, 1H), 2.51~2.56(m, 1H), 3.84~3.87(m, 1H), 4.03~4.07(m, 2H)

EXAMPLE 3

(2R,3R)1-azido-2-hroxy-3,4-isopropylidenebutane-2,3,4-triol (2b)

(2R,3R)-3,4-epoxy-1,2-O-isopropylidenebutane-1,2-diol (32.9 g) was dissolved in the mixture of 410 ml of ethanol and 40 ml of water. 85.4 ml of methyl formate was added to the solution and then 40 ml of water and 36.9 g of $NaN_3$ were added to the solution. The solution was stirred at 50~60° C. for 6 hours. At the end of the reaction, the ethanol was distillated under reduced pressure and the solution was diluted with 300 ml of water and was extracted three times with 300 ml of methylene chloride. The resultant solution was treated with $Na_2SO_4$ anhydride and distillated under reduced pressure. A light yellow liquid compound of (2S,3S)1-azido-2-hydroxy-3,4-isopropylidenebutane- 2,3,4-triol (2b) was obtained (40.7 g, yield: 95%).

EXAMPLE 4

(2S,3S)1,2-O-isopropylidene-3,4-(t-butoxycarbonyl) imino-butane-1,2-diol (Ib)

(2S,3S)1-azido-2-hydroxy-3,4-isopropylidenebutane-2,3,4-triol (40.6 g) was dissolved in 800 ml of acetonitrile and 56.9 g (1 equivalent) of $PPh_3$ was added to the solution. After the solution was stirred at room temperature for 1 hour, it was stirred with reflux at an increased temperature for 12 hours. The solution was cooled down to room temperature and the solvent was distillated under reduced pressure. 200 ml of 1,4-dioxane and 200 ml of water were added to the resultant. 36.4 g (2 equivalents) of $NaHCO_3$ and $(Boc)_2O$ of 50.4 ml (1 equivalent) were added to the solution respectively. After the solution was stirred at room temperature for 1 hour, the solvent was distillated under reduced pressure. The resultant was diluted with 250 ml of diethyl ether and washed with 250 ml of water. The separated ether layer was treated with $Na_2SO_4$ anhydride and then distillated under reduced pressure. The titled compound of (2S,3S)1,2-O-isopropylidene-3,4-(t-butoxycarbonyl)imino-butane-1,2-diol was obtained as a white liquid (50.1 g, yield: 95%).

$[\alpha]_D^{25}$=−45.14(Cl, $CHCl_3$)

1H-NMR (300 MHz, $CDCl_3$): δ1.35(s, 3H), 1.45(s, 9H), 1.46(s, 3H), 2.14(d, 1H), 2.35(d, 1H), 2.47~2.52(m, 1H), 3.74~3.80(m, 1H), 3.98~4.03(m, 1H), 4.16~4.21(m, 1H)

II. Synthesis of Aziridine Derivative of Formula (II)

EXAMPLE 5

(2R,3S)-1,2-O-isopropylidene-3-(t-butoxycarbonyl)-amino-4-phenylbutane (6)

The mixture of (2R,3S)-1,2-O-isopropylidene-3,4-(t-butoxycarbonyl)imino-butane-1,2-diol (50 g) and 308 ml of toluene was cooled down to −10° C. in the presence of $N_2$ and $CuBr.Sme_2$ (2.1 g) and 154 ml of PhMgCl (2M in THF) was added to the mixture respectively in the temperature of below −10° C. After the mixture was stirred in the temperature of below −10° C. for 1 hour, it was added to 308 ml of $NH_4Cl$ solution (33 g of $NH_4Cl$) and extracted by 300 ml of toluene. A white solid compound of (2R,3S)-1,2-O-isopropylidene-3-(t-butoxycarbonyl)-amino-4-phenylbutane was obtained after distillation under reduced pressure.

1H-NMR (300 MHz, $CDCl_3$): δ1.33(s, 3H), 1.40(s, 9H), 1.47(s, 3H), 2.79~2.96(m, 2H), 3.65(dt, 1H), 3.82~3.93(m, 2H), 4.09(dt, 1H), 4.82(d, 1H), 7.19~7.33(m, 1H)

EXAMPLE 6

(2R,3S)-3-(t-butoxycarbonyl)amino-4-phenyl-butane-1,2-diol (7)

(2R,3S)-1,2-O-isopropylidene-3-(t-butoxycarbonyl)-amino-4-phenylbutane (20 g) was dissolved in the mixture of 180 ml of methanol and 200 ml of water and 0.6 g (0.05 equivalent) of p-TsOH was added to the solution. The solution was stirred at 50° C. for 6 hours. After the solution was neutralized by adding 0.9 g (0.1 equivalent) of $K_2CO_3$, it was distillated under reduced pressure. The resultant was diluted with 200 ml of water, extracted twice by 200 ml of EtOAc, treated with Na$_2$SO$_4$ anhydride and distillated under reduced pressure. The titled compound of (2R,3S)-3-(t-butoxycarbonyl)amino-4-phenyl-butane-1,2-diol was obtained.

EXAMPLE 7

(2S,3S)-3-(t-butoxycarbonyl)amino-1,2-epoxy-4-phenylbutane (II)

(2R,3S)-3-(t-butoxycarbonyl)amino-4-phenoyl-butane-1,2-diol (21.8 g) was dissolved in 150 ml of EtOAc and cooled down to below 10° C. 6.9 ml (1.1 equivalent) of pyridine and 9 ml (1 equivalent) of benzoyl chloride were added to the solution and it was stirred at 5~10° C. for 2 hours. After addition of 7.2 ml (1.2 equivalent) of Ms-Cl, 21.6 ml (2 equivalents) of triethyl amine was added to the solution in the temperature of below 15° C. and it was stirred for 2 hours. The solution was washed by 150 ml of 1N HCl, 150 ml of 5% aq.NAHCO$_3$ and 150 ml of water and distillated under reduced pressure. 150 ml of 1,4-dioxane was added to the resultant and after the addition of 85 ml of 2M KOH, it was stirred at room temperature for 2 hours. After 150 ml of water was added to the solution, it was extracted by 150 ml of toluene and the toluene layer was washed by 150 ml of water. The layer was distillated under reduced pressure and the resultant was recrystallized in IPA/H$_2$O. A white crystal compound of (2S,3S)-3-(t-butoxycarbonyl)amino-1,2-epoxy-4-phenylbutane was obtained (mp: 125.6° C.).

$[\alpha]_D^{23}$=8.18 (Cl, MeOH)

1H-NMR (300 MHz, CDCl$_3$): δ1.39(s, 9H), 2.75~3.05(m, 5H), 3.71(broad s, 1H), 4.50(broad s, 1H), 7.2~7.38(m, 5H)

The above compound is intermediate for Amprenavir of the Glaxo-Wellcome.

EXAMPLE 8

(2R,3S)-3-(t-butoxycarbonyl)amino-1,2-epoxy-4-phenylbutane (II)

To the mixture of (2R,3S)-3-(t-butoxycarbonyl)amino-4-phenyl-butane-1,2-diol (44 g) and 400 ml of pyridine, 60 g (2 equivalents) of p-TsCl was added and the solution was stirred at 0° C. for 4 hours. After pH of the solution was adjusted 10 with 25% NaOH and it was stirred at 0° C. for 3 hours. 400 ml of methylene chloride was added to the solution and it was washed by 400 ml of 1N HCl, 400 ml of 5% aq.NaHCO$_3$ and 400 ml of water and was distillated under reduced pressure. A white crystal compound of (2R,3S)-3-(t-butoxycarbonyl)amino-1,2-epoxy-4-phenylbutane was obtained using a column chromatography.

1H-NMR (300 MHz, CDCl$_3$): δ1.37(s, 9H), 2.55~3.02(m, 5H), 4.10(s, 1H), 4.40(s, 1H), 7.16~7.35(m, 5H)

The above compound is the PI intermediate of the BMS company.

EXAMPLE 9

(1R)-1-benzyloxycarbonylamino-1-[(4R)-2,2-dimethyl-1,3-dioxalane-4-il]2-phenylthioethane (6)

13.3 ml (1.6 equivalent) of PhSH was drop-added to 5.2 g (1.6 equivalent) of NaH in 200 ml of THF at 0° C. under N$_2$ atmosphere.

After the generation of H$_2$ was stopped, the solution was stirred at room temperature for 30 minutes. The mixture of (2R,3S)-1,2-O-isopropylidene-3,4-(benzyloxycarbonyl) imino-butane-1,2-diol (22.5 g) and 100 ml of THF was slowly drop-added to the solution at room temperature. After the resultant solution was stirred at room temperature for 5 hours, 200 ml of water was added and followed by removal of THF and extraction by 200 ml of ether. The solution was treated with Na$_2$SO$_4$ anhydride and concentrated under reduced pressure. A crude compound of (1R)-1-benzyloxycarbonylamino-1-[(4R)-2,2-dimethyl-1,3-dioxalane- 4-il]2-phenyltioethane was obtained.

EXAMPLE 10

(2R,3R)-3-benzyloxycarbonylamino-4-phenylthio-1,2-butanediol (7)

The crude compound of (2R,3R)-3-benzyloxycarbonylamino-1-[(4R)-2,2-dimethyl-1,3-dioxalane-4-il]-2-phenylthioethane in the example 9 was dissolved in 200 ml of methanol and 100 ml of 1N HCl was added to the solution. The solution was stirred at 5° C. for 2 hours, concentrated under reduced pressure and extracted by 200 ml of ethyl acetate. The resultant solution was treated with Na$_2$SO$_4$ anhydride and concentrated under reduced pressure. A crude state compound of (2R,3R)-3-benzyloxycarbonylamino-4-phenyltio-1,2-butanediol was obtained.

EXAMPLE 11

(2S,3R)-3-benzyloxycarbonylamino-4-phenylthio-1-buteneoxide (II)

After the crude compound of (2R,3R)-3-benzyloxycarbonylamino-4-phenylthio-1,2-butanediol (13.3 g) from the example 10 was dissolved in 110 ml of EtOAc, 4 ml (1.3 equivalent) of pyridine and 5.3 ml (1.2 equivalent) of benzoyl chloride were added to the solution and it was stirred at 5~10° C. for 5 hours. 3.6 ml (1.2 equivalent) of Ms-Cl was added to the solution and 12.8 ml (2.4 equivalents) of triethyl amine was drop-added in the temperature of below 15° C. After the addition, it was stirred for 30 minutes. 1.5 ml (1 equivalent) of methanol was added to the solution and stirred at room temperature for 1 hour. The resultant solution was rinsed using 90 ml of 1N HCl, 90 ml of 5% NaHCO$_3$ and 50 ml of H$_2$O and distillated under reduced pressure. To the concentrated solution, 180 ml of 1,4-dioxane was added and the solution of 5.56 g (2.2 equivalent) of 85% KOH in 42 ml of H$_2$O was added. The resultant solution was stirred at room temperature for 2 hours. The solution was diluted with 280 ml of water and extracted using 280 ml of toluene. After the toluene layer was rinsed by 170 ml of H$_2$O, 170 ml of 5% NaHCO$_3$ and 170 ml of brine and treated with Na$_2$SO$_4$ anhydride, it was filtered and concentrated under reduced pressure. A white crystal compound of (2S,3R)-3-benzyloxycarbonylamino-4-phenylthio-1-buteneoxide was obtained by column chromatography using Hexane: EtOAc=2:1. mp 61.7° C.

$[\alpha]_D^{25}$=25.4 (cl, CHCl$_3$)

1H-NMR (300 MHz, CDCl$_3$): δ2.70~2.80(m, 2H), 3.00 (m, 1H), 3.22(d, 2H), 3.70(m, 1H), 5.08(s, 2H), 5.10(d, 1H), 7.10~7.20(m, 10H)

The above compound is Nelfinavir of the Agouron company.

As described above, the new aziridine derivatives according to the invention can be used as crucial intermediates for the synthesis of Amprenavir and Nelfinavir among the HIV protease inhibitors. (2S,3S)-3-(t-butoxycarbonyl)amino-1,2-epoxy-4-phenylbutane which is a crucial intermediate for the synthesis of Amprenavir can be prepared by accepting phenyl group. By accepting a phenylthio group instead of the phenyl group, (2S,3R)-benzyloxycarbonylamino-4-phenylthio-1-buteneoxide also can be prepared. The compound is a crucial intermediate for the synthesis of Nelfinavir. From the streoisomer of the compound, (2S,3S)-3-(t-butoxycarbonyl)amino-1,2-epoxy-4-phenylbutane, the synthesis of a HIV protease inhibitor with different structure with Amprenavir is possible.

The invention claimed is:

1. Aziridine derivatives of the following formula (Ia) or (Ib)

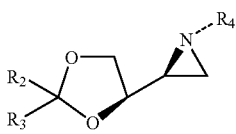
(Ia)

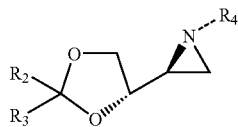
(Ib)

where $R_2$ and $R_3$ may be same or different and, respectively represent hydrogen, low alkyl or cycloalkyl, and $R_4$ is selected from the group consisting of aryl and amino protecting group.

2. The compound of claim 1, wherein said amino protecting group is selected from the group consisting of t-butoxycarbonyl, benzyloxycarbonyl, $CH_3$-Ph-$SO_2$—; $(Ph)_3C$, and FMOC(9-fluorenylmethyloxycarbonyl).

3. The compound of claim 1 wherein said $R_4$ represents a t-butoxycarbonyl.

4. The compound of claim 2, wherein said $R_4$ represents a t-butoxycarbonyl.

* * * * *